Figure 1:
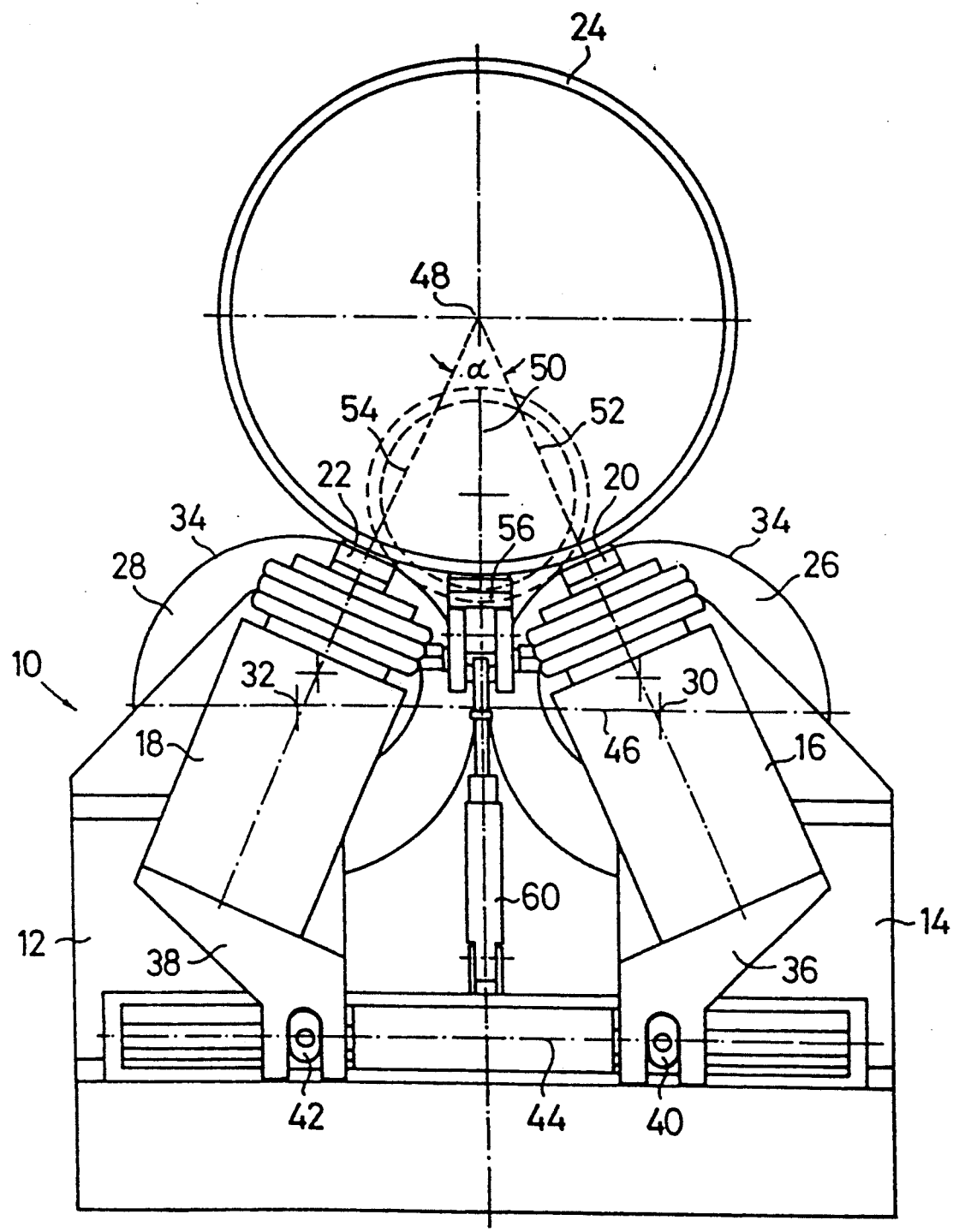

United States Patent [19]

Koch

[11] Patent Number: 5,279,160
[45] Date of Patent: Jan. 18, 1994

[54] ARRAY FOR NON-DESTRUCTIVE MATERIAL TESTING OF CYLINDRICAL WORKPIECES BY MEANS OF ELECTRODYNAMIC ULTRASONIC MEASUREMENT

[75] Inventor: Roman Koch, Hösbach, Fed. Rep. of Germany

[73] Assignee: Nukem GmbH, Fed. Rep. of Germany

[21] Appl. No.: 741,045

[22] Filed: Aug. 6, 1991

[30] Foreign Application Priority Data

Aug. 7, 1990 [DE] Fed. Rep. of Germany ... 9011477[U]

[51] Int. Cl.$^5$ .................... G01N 9/24; G01N 29.24; G01N 27/72; G01R 33/00
[52] U.S. Cl. ......................... 73/643; 73/622; 324/226; 324/262
[58] Field of Search ............... 324/226, 227, 235, 262; 73/620, 622, 633, 635, 643

[56] References Cited

U.S. PATENT DOCUMENTS

| | | |
|---|---|---|
| 3,182,490 | 5/1965 | Gibson . |
| 4,035,721 | 7/1977 | Lorenzi et al. . |
| 4,096,437 | 6/1978 | Kitzinger et al. . |
| 4,449,408 | 5/1984 | Brooks et al. ........................ 73/643 |
| 4,449,411 | 5/1984 | Suhl et al. ........................... 324/227 |
| 4,814,705 | 3/1984 | Saunderson ........................ 324/235 |
| 4,916,394 | 4/1990 | Thompson ......................... 324/262 |

OTHER PUBLICATIONS

Patents Abstracts of Japan, Sensitivity Calibration Method for Magnetic Flaw Detection Device, P-1069, Jun. 28, 1990, vol. 14, No. 301.

*Primary Examiner*—Walter E. Snow
*Attorney, Agent, or Firm*—Cushman, Darby & Cushman

[57] ABSTRACT

An array for non-destructive material testing of cylindrical workpieces such as pipes or ends thereof by means of leakage-flux measurement and if necessary electrodynamic ultrasonic excitation is proposed. A leakage-flux measuring head (56) used for leakage-flux measurement comprises at least two Hall probes (80) disposed along a line parallel and/or vertical to the magnetic field generated by a magnet (10) and forming at least one Hall probe line. In addition, the leakage-flux measuring head has at least two sliding blocks (94, 96, 98, 100) spaced apart and supportable on the workpiece, between which the Hall probes are disposed. The leakage-flux measuring head is also provided with a protective plate covering the faces of the Hall probes on the workpiece side.

2 Claims, 5 Drawing Sheets

ARRAY FOR NON-DESTRUCTIVE MATERIAL TESTING OF CYLINDRICAL WORKPIECES BY MEANS OF ELECTRODYNAMIC ULTRASONIC MEASUREMENT

The invention relates to an array for non-destructive material testing of cylindrical workpieces such as pipes or ends thereof by means of leakage-flux measurement and if necessary electrodynamic ultrasonic excitation, comprising at least one magnet such as a solenoid having pole shoes, at least one leakage-flux measuring head disposed outside the pole shoes, at least one supporting means serving to guide the workpiece such as rollers, and if necessary at least one electrodynamic converter head that can be provided with a cover on the workpiece side and can be supported on the workpiece.

A method and device for non-destructive testing of ferromagnetic materials, preferably cylindrical test specimens such as pipes or bars, is known from EP-B-0 071 147, in which the test specimen is surrounded by a rotating magnet having two pole shoes and in which the magnetic field generated by the magnet is used for leakage-flux measurement, with the magnetic field being used at the same time for electrodynamic excitation of an ultrasonic field in the test specimen, in order to perform both leakage-flux measurements and ultrasonic measurements using one and the same device.

The testing heads used for the respective measurements each comprise a measuring probe using which signals permitting conclusions to be drawn about faults and/or dimensions can be obtained. In the case of leakage-flux measurements, a magnetic leakage field extending outside the workpiece due to faults in the magnetized test specimen is detected using a magnetic field probe such as a Hall probe. In the case of electrodynamically excited ultrasonics, high-frequency pulse eddy currents are excited by means of a coil in the workpiece. A magnetic field effective at the same time in this area leads, together with the eddy currents, to the occurrence of Lorentz forces and magnetic and magnetostrictive forces acting on the lattice structure of the workpiece and causing ultrasonic waves. This principle illustrating the generation method can be reversed for reception. A suitable probe therefore comprises an exciter coil and a receiver coil to generate the high-frequency eddy currents and detect the ultrasonic waves respectively, with the probe being coverable by a cap if necessary to permit it to rest on the workpiece to be tested.

To achieve a high measuring density, a large number of probes must be disposed adjacently to one another. Measures of this type require a large amount of apparatus. The usual method is therefore to use fewer measuring probes, while putting up with the fact that high feed speeds for workpieces to be tested cannot generally be achieved to the extent required.

In order to test workpieces of differing diameter with the known devices, mechanically complex apparatus is required, particularly when the probes rotate around the workpiece. This is particularly the case for measurements in which electrodynamically excited ultrasonics are used.

One object of the present invention is to provide the possibility, using simple design means, of achieving a high measuring point density for leakage-flux measurements. It should be possible to test pipe ends too without difficulty using leakage flux. In addition, simple adaptation and alignment of the testing head(s) to differing workpiece diameters should be feasible. Finally, there should also be the possibility where required of carrying out simultaneously, with simple design means, leakage-flux measurements and electrodynamically excited ultrasonic measurements, with the density of the measuring points being individually adjusted and increased compared with known arrays.

The object is substantially attained in accordance with the invention in that the leakage-flux measuring head comprises at least two Hall probes disposed along a line parallel and/or vertical to the magnetic field generated by the magnet and forming at least one Hall probe line, in that the leakage-flux measuring head has at least two sliding blocks spaced apart and supportable on the workpiece and between which the Hall probes are disposed, and in that the leakage-flux measuring head is provided with a protective plate covering the faces of the Hall probes on the workpiece side.

In accordance with the invention, an array for non-destructive material testing using a leakage-flux measuring head is proposed, that is designed with several channels such that a high measuring point density can be achieved. The leakage-flux measuring head can here rest directly on the workpiece to be tested, so that high and reproducible signals from the Hall probes, which may be gradient Hall probes, can be obtained. As a result, impurities or burrs protruding from the workpiece cannot destroy the Hall probes themselves, since the latter are protected on the workpiece side by a protective plate preferably made of a copper/beryllium sheet.

In an embodiment of the leakage-flux measuring head in accordance with the invention for longitudinal fault testing, the line formed by the Hall probes is vertical to the magnetic field lines generated by the magnet in the pipe circumference direction. It is possible here to use two lines of Hall probes spaced adjacently to one another to increase the measuring point density.

In an embodiment of the measuring head for transverse fault testing, the Hall probe line is parallel to the magnetic field lines generated by the magnet in the longitudinal direction of the pipe.

In both embodiments, the individual Hall probes are so disposed that the active probe surface is always oriented vertical to the magnetic field lines.

Furthermore, a combination of parallel lines of Hall probes designed for longitudinal and for transverse fault testing respectively can be used in one leakage-flux measuring head, with the magnetization direction required in each case being used in two different test runs.

In a further embodiment of the invention, each Hall probe can be disposed detachably in the leakage-flux measuring head using a plug connection. Preferably however, all Hall probes or groups of Hall probes are disposed detachably as a unit in the leakage-flux measuring head, so that easy assembly is possible. This means that when faults occur, the Hall probes can be removed as a single unit from the measuring head and replaced by a new unit for subsequent testing.

Another embodiment of the invention provides for arrangement of the Hall probes or groups of Hall probes at least on a (first) board, which is in its turn connected by plug connectors to a base board. The leakage-flux measuring head is accordingly of modular design so that easy maintenance can be achieved.

The groups of Hall probes are disposed on first boards preferably parallel to one another and vertical to the magnetic field, whereas the base board, which has a plug connection to the local electronic system, i.e. that inside the testing head, is vertical to the field. The result of this measure is a compact unit.

In accordance with a further proposal, the first board is mounted in a detachable probe block extending from a base element of the leakage-flux measuring head, said block in its turn being covered on the workpiece side by a protective cap through which the sliding blocks pass.

The protective cap itself has, preferably centered and in the longitudinal direction, an opening through which the first board and the Hall probes pass in places and which is closed off by the protective plate to achieve a substantially flush outer surface on the workpiece side.

To ensure that the protective plate and possibly the Hall probes cannot be damaged even after an inadvertent slanted contact with the workpiece, a further solution proposal provides for the protective cap being passed through by sliding blocks arranged in pairs, between each of which blocks is provided at least one wear safety element. It is possible in this way to ascertain whether the sliding blocks are worn down to an extent requiring replacement.

To permit unproblematic adjustment to different workpiece diameters, without the need for expensive measures to align the leakage-flux measuring head, the latter has been designed adjustable for contact with the workpiece, preferably by means of a hydraulically or pneumatically operated lifting cylinder vertical to the longitudinal axis of the workpiece.

To achieve magnetization for longitudinal fault testing, the pole shoes of the magnet run symmetrically to the leakage-flux measuring head of the magnet and can in their turn be provided on the workpiece side with an electrodynamic converter head. Each electrodynamic converter head can be designed with several channels, i.e. comprising at least two probes, which in turn are covered on the workpiece side by a common protective plate. Accordingly, a design can be selected which—with the exception of the probes—has the same structure shown by the leakage-flux measuring head in accordance with the invention.

The pole shoes provided with the electromagnetic converter heads are preferably positioned against the workpiece using lifting cylinders integrated in the pole shoes.

The actuated lifting cylinders of the leakage-flux measuring head and of the electrodynamic converter heads can be operated both hydraulically and pneumatically. The cylinders and the actuation method are designed such that both the positioning of the measuring heads in relation to the workpiece and their withdrawal from the workpiece is possible.

In the device in accordance with the invention, the probes do not rotate around the workpiece, but the workpiece moves in relation to the probes. This means that the workpiece performs a translational and/or rotary movement in relation to the measuring heads. Accordingly, a translational movement of the test array can be overlaid with a rotary movement of the test specimen.

To permit alignment of the magnet in simple fashion to workpieces of differing diameter, which may have to be tested one after the other, the pole shoes of the magnet are designed adjustable. The pole shoes can be rotatable in each case about an axis coinciding with the axes of the supporting means designed as rollers, on which the workpiece is supported at least during rotary motion.

These design measures permit the electrodynamic converter head to be adjustable to a circle coinciding with the circumferential area of the rollers when a workpiece is resting on the latter. This in turn means that the electrodynamic converter head is always positionable in the area of the contact line of the workpiece using the supporting rollers.

It is possible here for both the electrodynamic converter heads and the leakage-flux measuring head to be withdrawn by the lifting unit behind the area of the support/drive rollers, to permit insertion of the workpiece when the measuring heads have been retracted during a translational motion of the testing unit too.

To allow adjustment of the pole shoes in relation to the workpiece, they have on their sides facing away from the workpiece a fork-shaped mounting which engages in pole shoe adjustment drivers that are adjustable along a straight line on the one hand parallel to the axes and on the other hand vertical to the workpiece longitudinal axis.

The drivers, which can be disposed on a spindle, for example, are moved synchronously and symmetrically to a plane containing the leakage-flux measuring head either towards or away from one another, so that the pole shoes are swivelled away from or towards one another respectively.

The spindles can be driven here by a drive motor equipped with a position pickup, so that automatic setting to a required pipe diameter is possible. If adjustment is performed using a hand crank, adapters designed as stops are provided against which the drivers are positioned and clamped.

The device in accordance with the invention permits not only longitudinal but also traverse faults to be determined. For measurement of the latter, it is necessary for the pole shoes of a magnet to be at a distance from one another along the longitudinal axis of the workpiece.

It is not essential for each pole shoe to be allocated an electrodynamic converter head, however each pole shoe is preferably provided with one to achieve a high measuring density.

It is of course possible for the device in accordance with the invention to be operated for a leakage-flux fault test only, using correspondingly designed pole shoe heads and also without electrodynamic converter heads.

Further details, advantages and features of the invention are given not only in the claims and the features stated therein—singly and/or in combination—but also in the following description of a preferred embodiment to be seen in one of the drawings.

Figure 2:
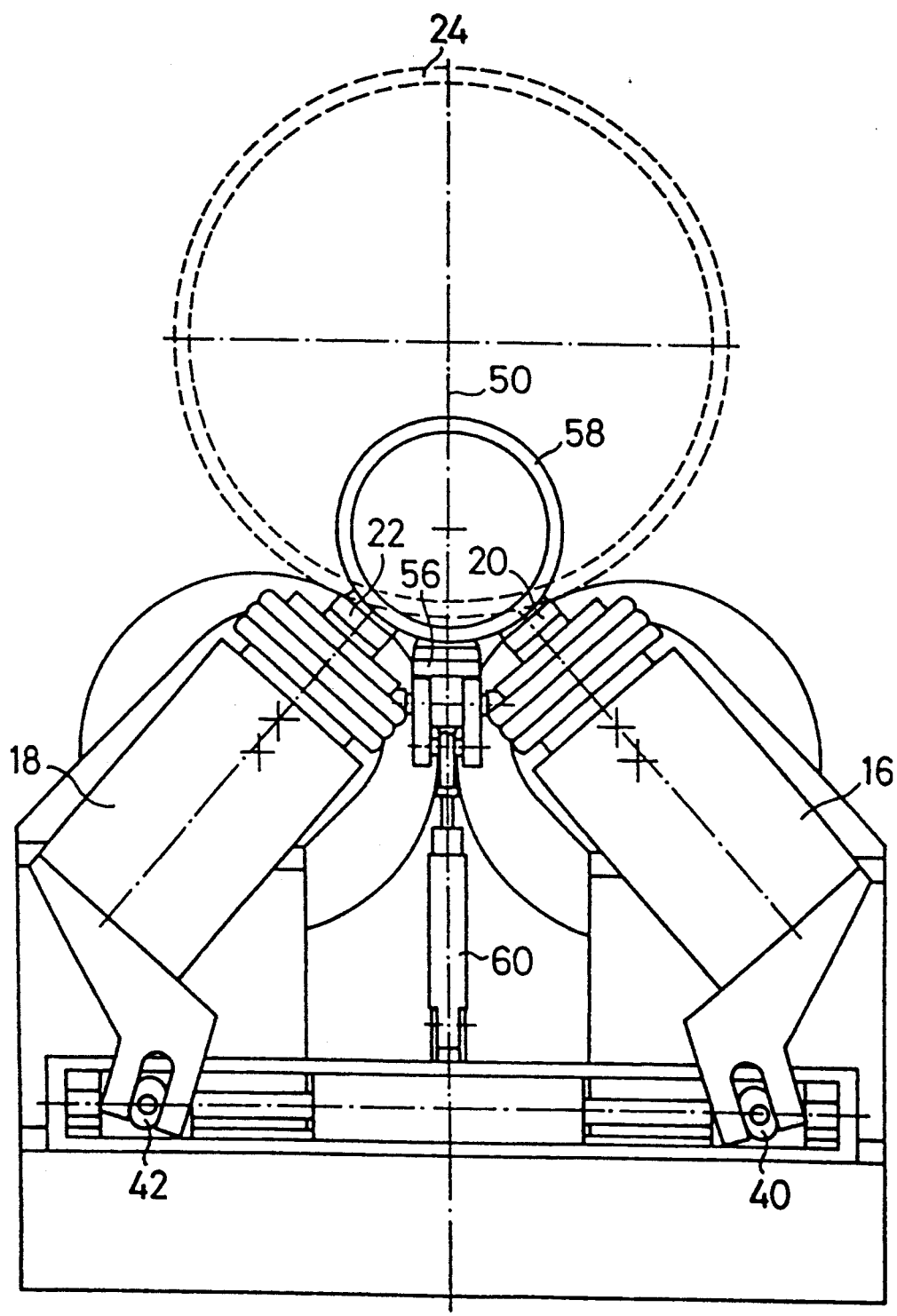
Figure 3:
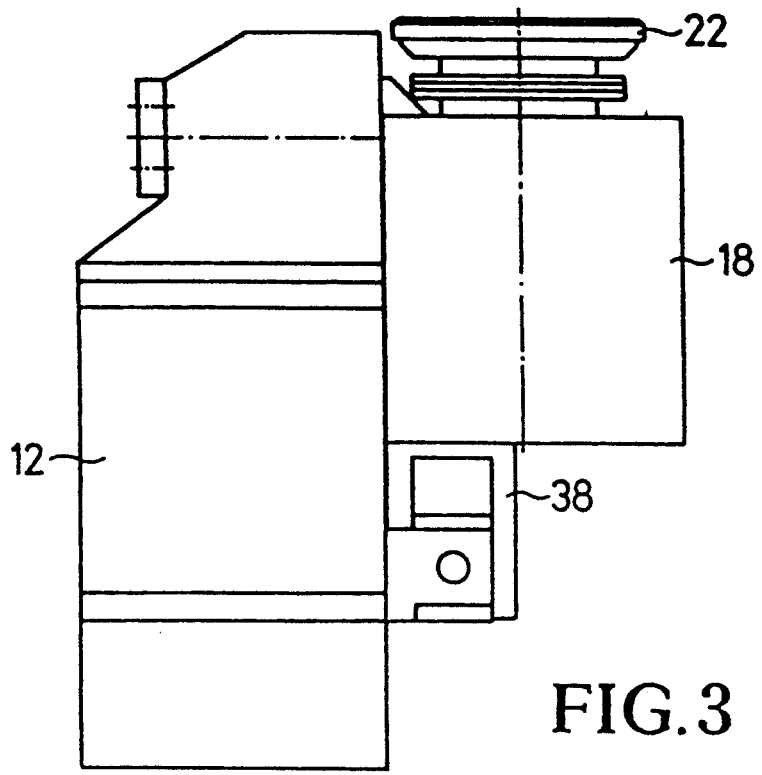
Figure 4:
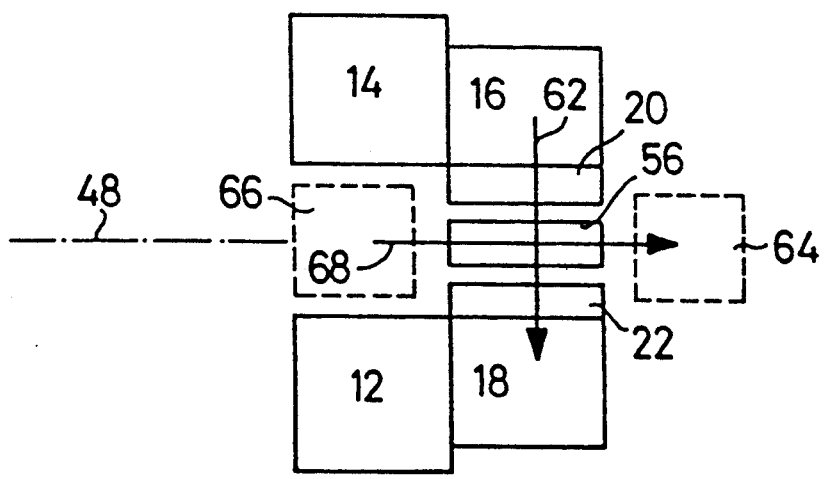
Figure 5:
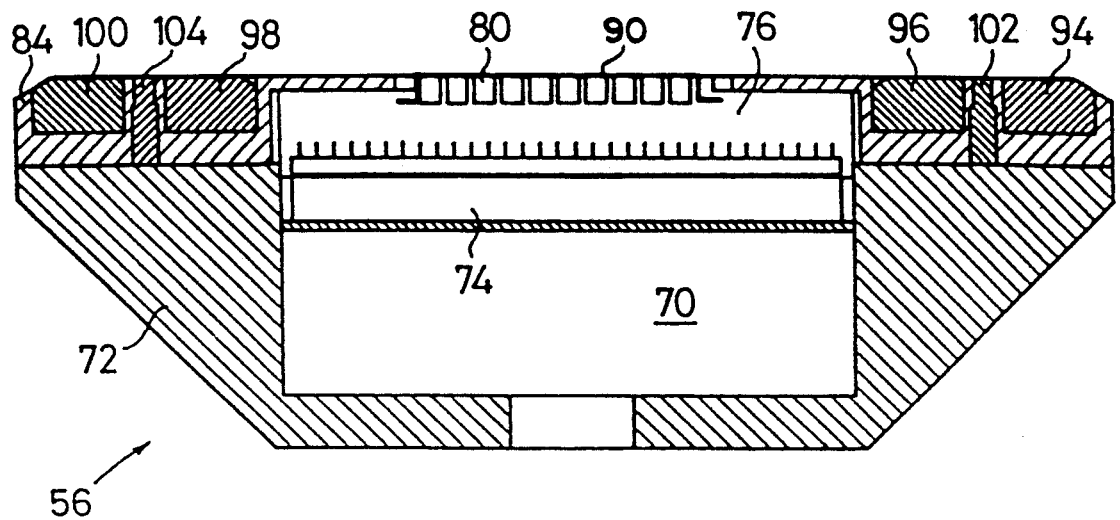
Figure 6:
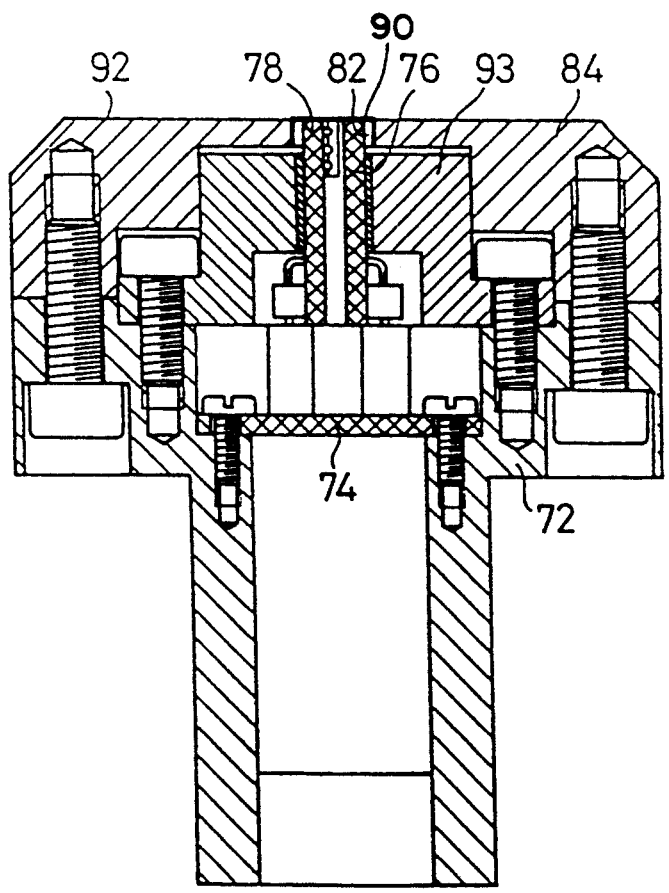
Figure 7:
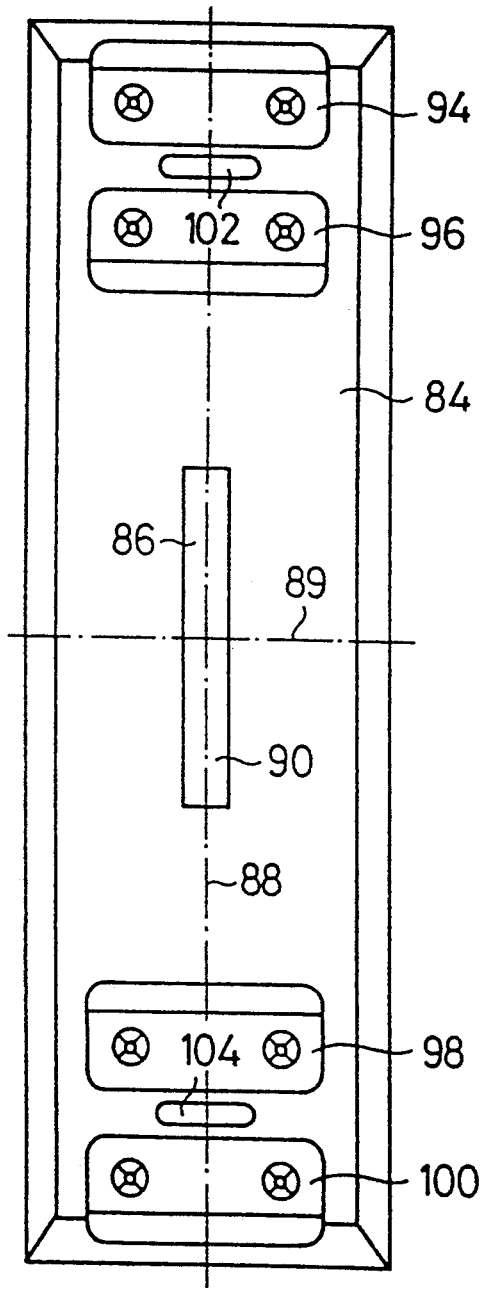
Figure 9:
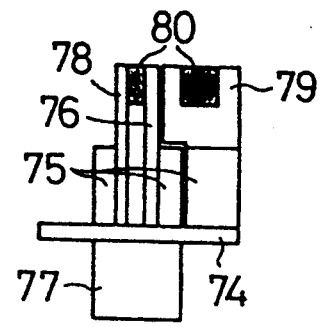
Figure 8:
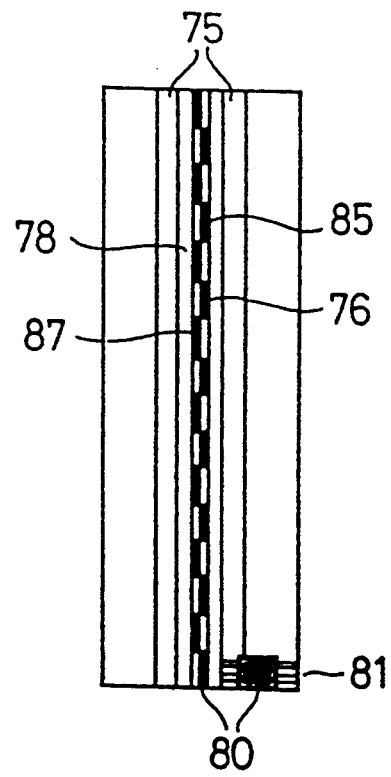

In these drawings,

FIG. 1 shows a section through an array in accordance with the invention for non-destructive testing of a large-diameter pipe, FIG. 2 shows the array in accordance with FIG. 1, however aligned for testing a smaller-diameter pipe, FIG. 3 shows a side view of a section of the array according to FIGS. 1 and 2, FIG. 4 shows a diagrammatic drawing of an array for longitudinal and transverse fault testing and testing using electrodynamically excited ultrasonics, FIG. 5 shows a longitudinal section through a leakage-flux measuring head, FIG. 6 shows a cross-section through a leakage-flux measuring head according to FIG. 5, FIG. 7 shows a plan view of the leakage-flux measuring head according to FIGS. 5 and 6, FIG. 8 shows a plan view of a board array, and FIG. 9 shows a front view of the board array as per FIG. 8.

A diagrammatic drawing of an array for non-destructive testing of cylindrical workpieces using both electrodynamically excited ultrasonics and leakage flux is shown in front view in FIGS. 1 and 2.

The main elements of the array are an electromagnet (10) with magnetic field coils (12) and (14), and adjustably designed pole shoes (16) and (18) having on their faces electrodynamic converter heads (20) and (22) restable on the outer surface of a large-diameter pipe (24) to be tested.

The workpiece (24) is supported on rollers (26) and (28) whose rotation axes are numbered (30) and (32).

The pole shoes (16) and (18) are rotatable about axes that coincide with the axes of the rollers (26) and (28), i.e. with their axes (30) and (32). The result of this is that the electrodynamic converter heads (20) and (22) can always engage with the workpiece outer face in a linear area on which the workpiece (24)—offset in the longitudinal direction—rests on the rollers (26) and (28).

The fact that the pole shoes (16) and (18), which double as a probe positioning mechanism, are rotatable about the axes (30) and (32) means that the testing heads (20) and (22) move on a circle (34) and (37) respectively, corresponding to that predetermined by the circumferential area of the rollers (26) and (28) respectively.

In order to move the pole shoes (16) and (18) on the circle (34) and (37) predetermined by the rollers (26) and (28), the pole shoes (16) and (18) have on their sides facing away from the workpiece (24) fork-shaped mountings (36) and (38) into which drivers (40) and (42) can be inserted that are adjustable along a straight line (44). The straight (44) runs parallel to the straight (46) running through the axes (30) and (32) and vertical to the workpiece longitudinal axis (48).

The drivers (40) and (42) can be disposed on a spindle and moved in the same direction towards or away from one another, i.e. symmetrically to an angle bisector (50) of the angle Δ enclosed by the lines (52) and (54) extending from the center point of the pipe (24) to the contact surfaces of the rollers (26) and (28) or of the testing heads (20) and (22).

The spindles can be driven here by a drive motor equipped with a position pickup, so that automatic setting to a required pipe diameter is possible. If adjustment is made using a hand crank, adapters designed as stops are provided against which the drivers are positioned and clamped.

In addition, a leakage-flux measuring head (56) is adjustably disposed along the angle bisectors (50), its design being described in further detail below.

Using the leakage-flux measuring head (56), it is possible to determine longitudinal faults in the pipe (24). The thickness of the pipe (24) itself can be measured using the electrodynamic converter heads (20) and (22).

In the array shown in FIG. 1, the pipe (24) can be rotated, and if necessary the mechanism containing the testing heads (20), (22) and (56) and the magnet and the adjusting unit for the pole shoes (16) and (18) can at the same time be moved as a single unit in the direction of the longitudinal axis (48) of the pipe (24).

Alternatively, the pipe (24) can rotate and perform a translational motion at the same time with the testing device stationary.

With the array according to FIG. 1, not only longitudinal fault and wall thickness measurements as already mentioned can be performed, but it is also possible to test the ends of the pipe (24).

The array shown in FIG. 2 corresponds to that in FIG. 1, but with the pipe (58) tested having a smaller diameter than the pipe (24). A comparison of the drawings shows that the parting movement of the drivers (40) and (42) moves the pole shoes (16) and (18), and hence the electrodynamic converter heads (20) and (22), towards one another to make contact with the outer surface of the pipe (58).

The leakage-flux measuring head (56), which is lowered by a lifting cylinder (60) operated hydraulically or pneumatically, for example, moves symmetrically between the electrodynamic converter heads (20) and (22), i.e. along the bisectors (50).

In spite of a change in the diameter of the pipe (58), it is not necessary to adjust the height of the testing unit. The only action needed is the alignment of the leakage-flux measuring head (56) to the new workpiece using the lifting cylinder (60) or an element with the same effect. The electrodynamic converter heads (20) and (22) must be adjusted accordingly.

FIG. 3 is a side view of the array shown in FIGS. 1 and 2. Shown are the coil (12) of the electro-magnet (10), the pole shoe (18) with the electrodynamic converter head (22), which can have several measuring probes disposed adjacently and covered by a common protective plate for testing in several channels, and the fork-shaped end section (38) engaging in the driver (42) for swivelling the pole shoe (18).

FIG. 4 is a diagrammatic drawing of the array according to FIGS. 1 to 3, and expansion possibilities thereof.

With the array described above, a magnetic field is generated that is represented by the arrow (62) and that is vertical to the pipe longitudinal axis (48). This is achieved using the magnet coils (12) and (14) of the electro-magnet with the rotatably designed pole shoes (16) and (18) and the electrodynamic converter heads (20) and (22) disposed thereon.

Using the leakage-flux measuring head (56), longitudinal faults of the workpiece can be determined.

To detect transverse faults at the same time, a magnetic field represented by the arrow (68) is generated by magnetic coils (64) and (66) that is parallel to the longitudinal axis (48) of the workpiece. As a result, the leakage-flux measuring head (56) can determine transverse faults in addition to longitudinal ones, provided that appropriate probes are disposed in the leakage-flux measuring head (56).

The leakage-flux measuring head in accordance with the invention has a structure as made clear in principle in FIGS. 5 to 7. In a square-shaped recess (70) of a base element (72), a base board (74) is disposed in the horizontal direction, by means of which the cable connection to the local electronic system is made using a plug connectors (77). Vertical hereto are boards (76) and (78), connectable to the base board (74) by plug connectors (75). The boards (76) and (78), also designated as first boards, are provided with gradient Hall probes, one of which is numbered (80) as an example.

As FIG. 5 in particular shows, a large number of Hall probes are disposed next to one another, so that a line (86) of Hall probes is obtained that runs along a line (88) in the embodiment, this line in turn running parallel to the longitudinal axis (48) of the workpiece to be tested.

The arrangement of the Hall probes (80) on the boards (76) and (78) designated as first boards in relation to the plug connection is selected such that two parallel and spaced Hall probe lines (85) and (87) for longitudinal fault testing can be set up (see FIG. 8 in particular) with the same board type simply by appropriate insertion on the base board (74). It is thus possible to increase the maximum packing density determined by the housing form and the connection contacts, and hence the measuring point density.

It is possible to determine longitudinal faults using the leakage-flux measuring head (56) in accordance with the embodiment in FIGS. 5 to 7. Alternatively, it is possible to fit the probes in the leakage-flux measuring head (56) transverse, i.e. vertical, to the arrangement shown, so that transverse faults too can be determined when the necessary magnetic field is generated. Another alternative is to dispose probes both in the longitudinal direction and transverse thereto in the same measuring head in order to permit both longitudinal and transverse fault testing.

This is shown in FIGS. 8 and 9. The Hall probe lines (85) and (87) contain Hall probes spaced apart whose active surfaces should be oriented vertical to the magnetic field lines. In this case the Hall probes extending from the first boards (76) and (78) are aligned to one another such that a tight "Hall probe line" is obtained in the side view (viewed from the left or right in FIG. 8).

A transverse fault Hall probe line (81) comprising two Hall probes (80) one behind the other as in FIG. 8 can extend from a further "first" board (79) vertical to the "first" boards (76) and (78). The active surfaces of the probes (80) extend also vertical to the magnetic field lines running in the workpiece longitudinal axis for transverse fault measurements.

The Hall probes (58) disposed along the straight (86) in FIG. 7 pass through an opening (82) in a protective cap (84) extending from the base element (72), as shown in FIGS. 6 and 7.

On the workpiece side, the opening (82) is covered by a protective plate (90) flush with the outer surface (92) of the protective cap (84) on the outside. The protective plate (90) is preferably a copper/beryllium sheet.

The protective cap (84) can be screwed to the base element (72).

The first boards (76) and (78) on the one hand having the gradient Hall probes (80) and on the other hand being connected to the base board (74) by plug connectors are in turn held by a probe block (93) which can also be screwed to the base element (72). This permits the probe block (93) to be replaced as a complete unit together with the boards (76) and (78) and the Hall probes.

At the end of the Hall probe line (86), the protective cap (84) has pairs of sliding blocks (94), (96) and (98), (100) passing through it.

The sliding blocks (94), (96), (98), (100) protrude slightly above the outer surface (92) of the protective cap (84). Accordingly, the sliding blocks (94), (96), (98), (100) contact the workpiece when the latter is set down, so that the protective cap (84) and hence the protective plate (90) are protected.

Wear safety contacts (102) and (104) are disposed between the sliding blocks (94), (96) and (98), (100) respectively. Each wear safety contact (102) and (104) has a helically or spirally arranged wire embedded in a sealing compound. The upper surface of the wire is lower than the free area of the respective sliding block (94), (96) and (98), (100). If the sliding blocks (94), (96), (98) and (100) are now unacceptably worn, further abrasion will destroy the wire in each wear safety contact (102) and (104). As a result, an alarm signal is given to indicate that the sliding blocks are unacceptably worn. They can then be replaced.

I claim:

1. An array for non-destructive testing of cylindrical workpieces such as pipes or ends of pipes by means of at least electrodynamic ultrasonic excitation, comprising:
   at least one magnet having pole shoes; and
   at least one supporting means for supporting and guiding the workpieces;
   said pole shoes being rotatable around axes parallel to a longitudinal axis of one of the workpieces being guided by said supporting means, said pole shoes being provided with at least one electrodynamic transducer resting on said one of said workpieces in a contact area, said supporting means comprising rollers, said rollers being rotatable about axes which coincides with axes of rotation of said pole shoes, said one of said workpieces being supported on each roller in a linear area of lower circumferential surface of said one of the workpieces, and said linear area, offset in a longitudinal direction of said one of the workpieces, corresponding to said contact area of said electrodynamic transducer.

2. An array as set forth in claim 1 in which said pole shoes have, on their sides facing away from said workpiece, fork-shaped mountings which engage in drivers for rotating said pole shoes about said axes, said drivers being movable along a straight line which is parallel to the axes of rotation of said pole shoes and perpendicular of the longitudinal axis of the workpiece.

* * * * *